United States Patent
Durham et al.

(10) Patent No.: US 11,062,048 B1
(45) Date of Patent: Jul. 13, 2021

(54) DATA STRUCTURE THAT FACILITATES DIGITAL RIGHTS MANAGEMENT

(71) Applicant: Allscripts Software, LLC, Raleigh, NC (US)

(72) Inventors: Ryan Durham, Litchfield, IL (US); Jacob William Baird, Collinsville, IL (US); Travis Lee Yates, Belleville, IL (US); Peter Dylan Ross, Collinsville, IL (US)

(73) Assignee: Allscripts Software, LLC, Raleigh, NC (US)

( * ) Notice: Subject to any disclaimer, the term of this patent is extended or adjusted under 35 U.S.C. 154(b) by 220 days.

(21) Appl. No.: 15/910,544

(22) Filed: Mar. 2, 2018

(51) Int. Cl.
*G06F 21/62* (2013.01)
*G16H 10/60* (2018.01)
*G06F 16/14* (2019.01)
*G06F 16/9535* (2019.01)

(52) U.S. Cl.
CPC ........ *G06F 21/6245* (2013.01); *G06F 16/148* (2019.01); *G06F 16/9535* (2019.01); *G16H 10/60* (2018.01)

(58) Field of Classification Search
CPC ............................ G06F 21/6245; G06F 16/24
See application file for complete search history.

(56) References Cited

U.S. PATENT DOCUMENTS

| 5,508,912 | A | * | 4/1996 | Schneiderman | ...... G06F 19/325 705/3 |
| 10,061,654 | B1 | * | 8/2018 | Patwardhan | ........ G06F 11/1464 |
| 2013/0097086 | A1 | * | 4/2013 | Dala | ..................... G06F 21/602 705/51 |
| 2015/0269214 | A1 | * | 9/2015 | Avati | ................. G06F 16/2358 707/689 |
| 2017/0091388 | A1 | * | 3/2017 | Zolla | ..................... G06F 16/254 |
| 2017/0091397 | A1 | * | 3/2017 | Shah | ..................... H04L 63/107 |
| 2018/0114594 | A1 | * | 4/2018 | Bessette | ................. G06Q 50/24 |

* cited by examiner

*Primary Examiner* — Dao Q Ho
(74) *Attorney, Agent, or Firm* — Medley, Behrens & Lewis, LLC

(57) ABSTRACT

Described herein are various technologies pertaining to creating and modifying a computer-readable file for a patient in response to receiving data about the patient. The computer-readable file is modified by appending a child file record to the computer-readable file, identifying a parent file record for the child file record in the computer-readable file, and storing a pointer in the parent file record to the child file record. The child file record comprises the data about the patient, an initially empty pointer portion, and an attribute of a user that has permission to access the data about the patient. The pointer portion may be later modified to include pointers to subsequently added file records in the computer-readable file.

20 Claims, 12 Drawing Sheets

DATA STRUCTURE THAT FACILITATES DIGITAL RIGHTS MANAGEMENT

BACKGROUND

Electronic health record (EHR) systems are systems utilized by healthcare organizations to generate and maintain health records for patients. As a patient visits different healthcare organizations using different EHR systems, his or her medical records become scattered across various EHR systems. This leads to "silos" of health data for the patient that can be difficult to access. For instance, a patient may make an emergency room visit, and a hospital system that operates the emergency room may use a first EHR system to generate and maintain patient records. Sometime thereafter, the patient may visit an orthopedic surgery center, where the center utilizes a second EHR system to generate and maintain patient records. Conventionally, a healthcare worker at the orthopedic surgery center is unable to access the records about the patient generated and stored by the first EHR system. Instead, the healthcare worker must contact the hospital that operates the emergency room, whereupon the hospital will provide a summary of a patient record of interest to the healthcare worker at the orthopedic surgery center (presuming that the patient consented to the sharing of the patient record).

Further, using conventional technology, it may be difficult to acquire data about a patient from a patient record generated by a single EHR system. More specifically, aggregation of data from EHR system databases that are developed over extended periods of time often leads to bifurcation of data entries within a patient record (generated or stored via the EHR system) due to gradual pace of change, feature alterations, bug fixes, loss of platform support, employee turnover at EHR system vendors, and so forth. Therefore, in an example, a patient record may be stratified across different records in the EHR system; hence, to retrieve data for a patient from the EHR system, multiple queries may need to be executed over multiple databases of the EHR system, which is computationally expensive and time consuming. Additionally, many elements of the patient record may be duplicated across different records in the EHR system, thus leading to inefficient use of storage space within the EHR system.

Moreover, when an end user is navigating to different parts of the patient record within a graphical user interface (GUI) of the EHR system, time consuming screen refreshes may be required, as only portions of the patient record are being pulled from one or more databases based upon a location of the end user in the GUI.

This paradigm of record generation and storage, where data is retained in individual silos, is relatively inefficient and may be detrimental to the patient. For example, during the aforementioned emergency room visit, a healthcare worker in the emergency room may have performed a blood test on the patient, wherein the blood test results (e.g., "normal" or "abnormal") are based upon the values of ten separate blood parameters. A surgeon at the orthopedic surgery center may be interested in a particular one of those parameters; for example, iron count in the blood of the patient. Conventionally, however, the EHR system at the hospital is configured to generate a summary rollup of the blood test results (which may be based upon multiple portions of the patient record retrieved from different databases of the EHR system at the hospital), where the summary rollup may indicate that the blood test results are "normal." The summary rollup, however, does not include the detail desired by the surgeon. Hence, the surgeon may order another blood test to be performed on the patient, which can be costly and generally undesired by the patient.

SUMMARY

The following is a brief summary of subject matter that is described in greater detail herein. This summary is not intended to be limiting as to the scope of the claims.

Described herein are various technologies pertaining to generating a computer-readable file for a patient, wherein the computer-readable file is created or modified in response to receiving data about the patient. As will be described in greater detail herein, an electronic health record application (EHR) can create and/or modify the computer-readable file. With more specificity, upon receipt of data about the patient, the EHR identifies a parent file record for the data within the computer-readable file. In the event that no parent file record exists (i.e., this is the first time the EHR has received data about the patient), the EHR can create an initial file record for the patient. After identifying a parent file record for the data (or after creating the parent file record), the EHR generates a child file record in the computer-readable file that makes up a portion of the computer-readable file. The child file record may include: 1) a marker that identifies a beginning of the child file record; 2) data related to a patient encounter; 3) an (initially empty) pointer portion that can be later populated with pointers to subsequently added file records within the computer-readable file; 4) an access portion that identifies an attribute of a user having permission to access the data about the patient; and 5) a checksum. The EHR can then append the child file record to an end of the computer-readable file. The EHR modifies the parent file record for the child file record by storing a pointer to the child file record in the parent file record. It is understood that the child file record may serve as a parent file record for new data about the patient that is received by the EHR after the above-referenced data is received.

Subsequently, the EHR may generate or receive second data about the patient that is to be included in the computer-readable file. In response to generating or receiving the second data, the EHR identifies the parent file record (e.g., based upon an identifier for the patient). The EHR then generates a second child file record and appends the second child file record to the computer-readable file as described above. The second child file record may include: 1) a marker that identifies a beginning of the second child file record; 2) second data related to a patient encounter; 3) an initially empty pointer portion that can later populated with pointers to subsequently added file records within the computer-readable file; 4) an access portion that identifies an attribute of a user having permission to access the second data about the patient; and 5) a checksum. The EHR may then modify the parent file record for the second child file record by storing a pointer to the second child file record in the parent file record for the second child file record.

In another example, the EHR may generate or receive third data that is to be appended to the second data about the patient. In response to generating or receiving the third data about the patient, the EHR can identify the parent file record for the third data. In this example, the parent file record for the third data is the second child file record. The computing system can then create a third child file record and append the third child file record to the computer-readable file. The third child file record may include: 1) a marker that identifies a beginning of the third child file record; 2) a diff, wherein the diff contains only data within the third data about the patient that differs from the second data; 3) an initially empty pointer portion that can be later populated with pointers to subsequently added file records within the computer-readable file; 4) an access portion that identifies an attribute of a user having permission to access the third child file record; and 5) a checksum. The computing system may then modify the parent file record for the third data (i.e., the second child record) to include a pointer to the third child file record.

The computing system may then append a map portion and a file access portion to the computer-readable file. The map portion may comprise pointers to the parent file for the child file record, the child file record, the second child file record and/or the third child file record. The read model is configured to optimize retrievals when it is predicted that a read is likely. The file access portion comprises an attribute of at least one user that has permission to access the computer-readable file. The EHR may then cause the computer-readable file to be persistently stored in computer-readable storage, wherein the EHR can subsequently access and/or modify the computer-readable file. The EHR may also transmit at least a portion of the computer-readable file to a client computing device in response to receiving a query from the client computing device, the query indicative of a file record in the computer-readable file.

The above summary presents a simplified summary in order to provide a basic understanding of some aspects of the systems and/or methods discussed herein. This summary is not an extensive overview of the systems and/or methods discussed herein. It is not intended to identify key/critical elements or to delineate the scope of such systems and/or methods. Its sole purpose is to present some concepts in a simplified form as a prelude to the more detailed description that is presented later.

DETAILED DESCRIPTION

Figure 1:
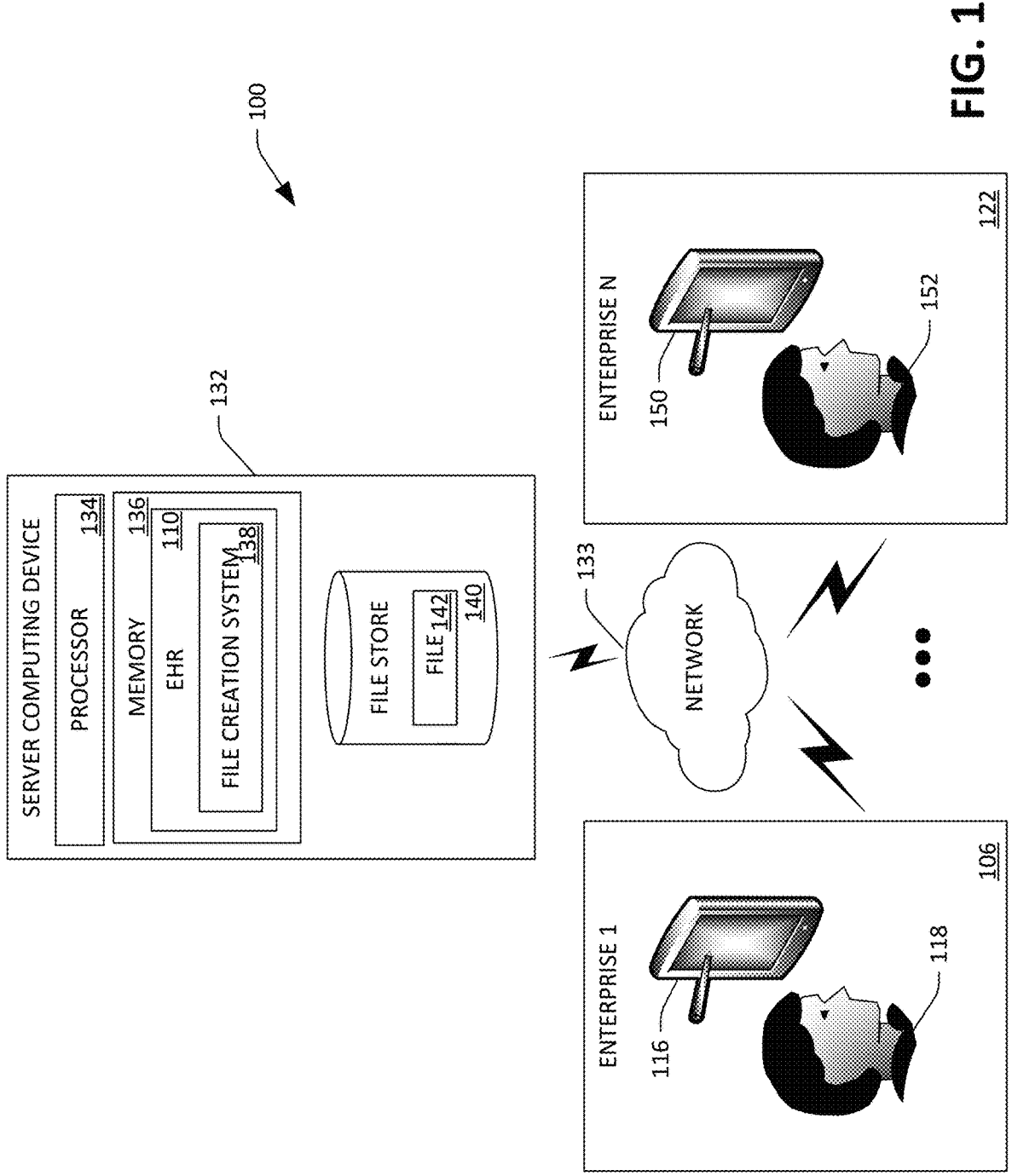
FIG. 1 is a functional block diagram of an exemplary computing system that facilitates generating a computer-readable file.

Various technologies pertaining to creating and modifying computer-readable files, as well as various technologies for locating records in such computer-readable files, are now described with reference to the drawings, wherein like reference numerals are used to refer to like elements throughout. In the following description, for purposes of explanation, numerous specific details are set forth in order to provide a thorough understanding of one or more aspects. It may be evident, however, that such aspect(s) may be practiced without these specific details. In other instances, well-known structures and devices are shown in block diagram form in order to facilitate describing one or more aspects. Further, it is to be understood that functionality that is described as carried out by certain system components may be performed by multiple components. Similarly, for instance, a component may be configured to perform functionality that is described as being carried out by multiple components.

Moreover, the term "or" is intended to mean an inclusive "or" rather than an exclusive "or." That is, unless specified otherwise, or clear from the context, the phrase "X employs A or B" is intended to mean any of the natural inclusive permutations. That is, the phrase "X employs A or B" is satisfied by any of the following instances: X employs A; X employs B; or X employs both A and B. In addition, the articles "a" and "an" as used in this application and the appended claims should generally be construed to mean "one or more" unless specified otherwise or clear from the context to be directed to a singular form.

Further, as used herein, the terms "component" and "system" are intended to encompass computer-readable data storage that is configured with computer-executable instructions that cause certain functionality to be performed when executed by a processor. The computer-executable instructions may include a routine, a function, or the like. It is also to be understood that a component or system may be localized on a single device or distributed across several devices. Further, as used herein, the term "exemplary" is intended to mean serving as an illustration or example of something, and is not intended to indicate a preference.

With reference to FIG. 1, an exemplary computing system 100 that facilitates creating and/or modifying a file for a patient is illustrated. The computing system 100 can include a server computing device 132. The server computing device 132 includes a processor 134 and memory 136, wherein the memory 136 includes an electronic health records application (EHR) 110 loaded therein. Generally, the EHR 110 is configured to facilitate creation, storage, and maintenance of health records for patients. As such, the EHR 110 comprises a file creation system 138 (described in greater detail below). The server computing device 132 additionally comprises a file store 140 that includes a computer-readable file 142 for a patient, wherein the EHR has access to the file store 140. While the file store 140 is illustrated as including a single computer-readable file, it is understood that the file store 140 can include (separate) files for many different patients.

The computing system 100 may further include a first client computing device 116 operated by a healthcare worker 118 in first enterprise 106. In an example, the first enterprise 106 may be a first healthcare organization, and can be or manage a hospital, an urgent care facility, a family doctor facility, etc. The first client computing device 116 is in communication with the server computing device 132 by way of a network 133 (e.g., the Internet). The first client computing device 116 is employed by the healthcare worker 118 to access the EHR 110. For instance, the first client computing device 116 may have a client EHR application installed thereon that interfaces with the EHR 110, wherein data can be transmitted between the client EHR and the EHR 110 to: 1) create and/or modify health records for a patient; and/or 2) retrieve information (e.g., files, records within files, etc.) from the file store 140. For example, the healthcare worker 118 can utilize the first client computing device 116 to set forth notes pertaining to a patient encounter, and the notes can be transmitted to the server computing device 132, wherein the EHR 110 can incorporate the notes into the computer-readable file 142 (described below).

The computing system 100 may also include an nth client computing device 150 operated by a second healthcare worker 152 in an nth enterprise 122. In an example, the nth enterprise 122 may be a healthcare organization, and can be or manage a hospital, an urgent care facility, a family doctor facility, etc. The nth client computing device 150 is in communication with the server computing device 132 by way of the network 133. The nth client computing device 150 is employed by the second healthcare worker 152 to access the EHR 110. For instance, the nth client computing device 150 may have a client EHR application installed thereon that interfaces with the EHR 110, wherein data can be transmitted between the client EHR and the EHR 110 to: to 1) create and/or modify health records for a patient; and/or 2) retrieve health records from the file store 140. For example, the healthcare worker 152 can utilize the nth client computing device 150 to enter thermometer readings taken over a range of time, and the thermometer readings can be transmitted to the server computing device 132, wherein the EHR 110 can incorporate the thermometer readings into the computer-readable file 142.

While the system 100 is depicted as both client computing devices 116 and 150 having access to the EHR 110, there are other architectures contemplated. For example, the server computing device 132 can execute separate instances of the EHR 110 for each enterprise—thus, the first client computing device 116 interfaces with a first instance of the EHR executing on the server computing device 132, while the nth client computing device interfaces with an nth instance of the EHR executing on the server computing device 132. In an exemplary implementation, these instances of the EHR may execute in different virtual machines. In other examples, the instances of the EHR can be executed separately without requiring different virtual machines. For purposes of ease of explanation, the client computing devices 116 and 150 will be described as accessing the EHR 110; it is to be understood, however, that in practice the client computing devices 116 and 150 will access and interact with different instances of the EHR 110.

Operation of the computing system 100 is now set forth. In an example, when a patient first visits the enterprise 106, a healthcare worker (e.g., the healthcare worker 118) can cause a file for the patient to be created in the file store 140. For instance, the healthcare worker 118 can enter identifying information and demographic information about the patient into a graphical user interface of the client EHR at the client computing device 116, such as name, date of birth, address, gender, and so forth. The client computing device 116 transmits this information to the EHR 110 executing on the server computing device 132, and the file creation system 138 creates the computer-readable file 142 for the patient in response to receiving such information from the client computing device 116. The newly created computer-readable file 142 includes an identifier for the patient (such as a medical record number) and a pointer portion that can be later populated with pointers to file records within the computer-readable file 142 as new file records are added to the computer-readable file 142. The computer-readable file 142 may also include a marker, a checksum, and an access portion (described below).

After the computer-readable file 142 for the patient has been generated, the healthcare worker 118 (or some other healthcare worker) can input data about the patient into the client computing device 116, wherein the data about the patient pertains to a patient encounter, and further wherein the data about the patient is input by way of the client EHR. The client computing device 116 transmits such data to the server computing device 132, whereupon the file creation system 138 identifies a parent file record for the data within the computer-readable file 142—the file creation system 138 identifies this parent file record by seeking through the computer-readable file 142. The parent file record can take different forms depending on the data. In one example, when the data about the patient is indicative of a type of allergy of the patient, the parent file record can be a file collection for allergies. A file collection is a file record that includes data about a category (e.g., allergies, problems) and pointers to file records that belong to the category. In another example, when the data about the patient is indicative of a follow-up visit to an initial visit to a healthcare facility, the parent file record can be a file record for the initial visit to the healthcare facility. Identifying a parent file record for the data about the patient may be accomplished by analyzing a "map" portion of the computer-readable file 142 (described below).

Responsive to identifying the parent file record for the data about the patient, the file creation system 138 can generate a child file record representative of the above-referenced patient encounter data received from the first client computing device 116. The child file record created by the file creation system 138 comprises the data about the patient received from the first client computing device 116, a pointer portion that can later be populated with pointers to other file records within the computer-readable file 142, and an access portion. As will be described in greater detail below, the first child file record can also include a marker and a checksum. It is to be understood that the access portion for the parent file record may differ from the access portion of the first child file record such that certain users (i.e., healthcare professionals) may have access to the parent file record, but not the child file record, and vice versa.

The file creation system 138 can then append the child file record to an end of the computer-readable file 142. Responsive to appending the child file record to the computer-readable file 142, the file creation system 138 can modify the parent file record for the child file record to include a pointer to the child file record. The file creation system 138 can also generate and append a map portion, a read model, and a file access portion to the compute-readable file 142. As will be described in greater detail below, the map portion includes a location of the child file record within the computer-readable file 142. The read model is configured to optimize retrievals when a read is predicted to be likely. The file access portion includes an attribute of at least one user that has permission to access the computer-readable file 142.

Subsequent to the patient visiting the first enterprise 106, the patient may visit the nth enterprise 122, wherein the second client computing device 150 creates second data for the patient that is indicative of the patient encounter with the nth enterprise 122. In an example, the visit to the nth enterprise 122 may be related to the visit to the first enterprise 106. The EHR 110 executing on the server computing device 132 can receive the second data about the patient from the second client computing device 150. The file creation system 138, in response to receiving the second data about the patient from the second client computing device 150, retrieves the computer-readable file 142 from the file store 140, decompresses and decrypts the computer-readable file 142, if necessary, deserializes the computer-readable file 142, and identifies an end of the most recently added file record in the computer-readable file 142.

The file creation system 138 then identifies a parent file record for the second data about the patient. In an example, the parent file record for the second data about the patient is the child file record described above. The file creation system 138 then generates a second child file record comprising the second data about the patient, a second pointer portion (initially empty), and an access portion. The second child file record can also include a second marker and a second checksum (described below). The file creation system 138 can then append the second child file record to the computer-readable file 142. Responsive to appending the second child file record to the computer-readable file 142, the file creation system 138 updates the pointer portion of the child file record to include a pointer to the second child file record. Responsive to including the pointer to the second child file record in the pointer portion of the child file record, the file creation system 138 can update the map portion, the read model, and/or the file access portion of the computer-readable file 142.

In certain cases, the second data about the patient may be an updated version of the first data about the patient. For example, the first data about the patient can comprise demographic information about the patient, such as name, sex, height, address, etc. The second data about the patient can be a modification of the first data about the patient. For instance, the second data about the patient may include an updated address, but otherwise may be the same as the first data about the patient. In these cases, instead of storing the entirety of the second data about the patient in the second child file record, the file creation system 138 can store only portions of the second data about that patient that are not duplicative of the first data ("a diff"). This reduces the space taken up by the second file record within the computer-readable file 142. For instance, if the data in the child file record is "A B C" and the second data is "A B," the data stored in the second child file record can be "–C," wherein the "–" indicates that the only difference between the data in first data about the patient and the second data about the patient is that "C" has been deleted. Additionally, by starting at the parent file record and subsequently accessing child file records of the parent file record, a computing device accessing the computer-readable file 142 can examine each individual change to the computer-readable file 142.

By way of another example, the visit to the nth enterprise may be unrelated to the first patient encounter. In this case, the parent file record for the second data about the patient is the initial file record for the patient described above. As such, responsive to appending the second child file record to the computer-readable file 142, the file creation system 138 updates the pointer portion of the initial file record to include a pointer to the second child file record. It is to be noted that the computer-readable file 142 for the patient is accessible to instances of the EHR corresponding to different enterprises, so long as the patient has authorized such access. Therefore, the separate enterprises 106 and 122 need not generate and maintain their own, siloed file for the patient. Instead, the file 142 is accessible to respective instances of the EHR 110 of the enterprises 106 and 122, and can be appended to by the instances of the EHR 110 of the enterprises 106 and 122. The structure of the computer-readable file 142, described below, allows for multiple instances of the EHR 110 to access and append to the computer-readable file 142 while only allowing an instance of the EHR 110 to be able to obtain data from the file 142 that it is authorized to obtain. Thus, the structure of the computer-readable file 142 addresses security concerns with having multiple instances of the EHR 110, corresponding to different enterprises, being able to access and modify the computer-readable file 142.

Figure 2:
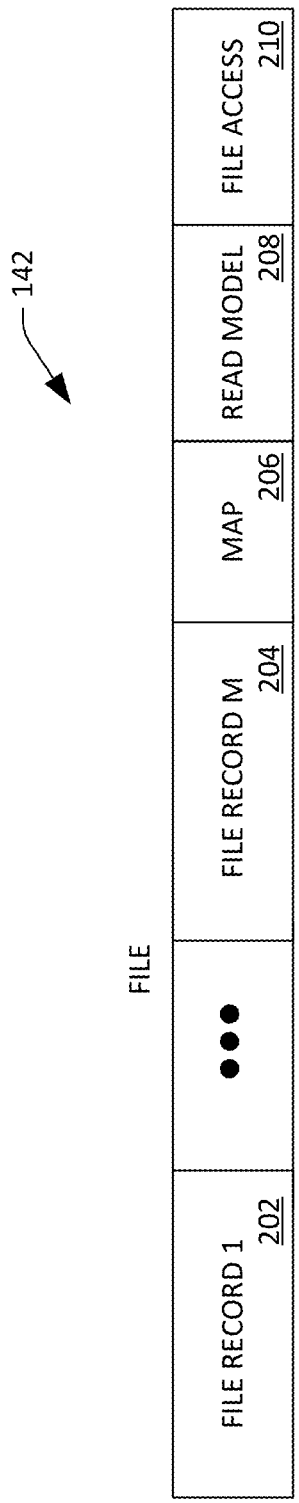
FIG. 2 is a schematic of an exemplary computer-readable file.

Referring now to FIG. 2, an exemplary schematic of the computer-readable file 142 is depicted. The computer-readable file 142 comprises a plurality of file records 202-204 that are appended to one another. The file records 202-204 are arranged in the computer-readable file 142 based upon when patient data was generated by the EHR 110. More specifically, the first file record 202 corresponds to first patient encounter data, while the mth file record 204 corresponds to mth patient encounter data that was created subsequent to the first patient encounter data. Therefore, the file records 202-204 are arranged in the computer-readable file 142 from oldest (at a beginning of the computer-readable file 142) to newest (at an end of the computer-readable file 142). Modification of the file records 202-204 is accomplished by identifying parent file records in the computer-readable file for new data received by the server computing device 132, appending additional file records reflective of the new data to the computer-readable file 142, and updating pointer portions of the file records 202-204 to include pointers to the additional file records.

The computer-readable file 142 further comprises a map portion 206 that is appended to the mth (last) file record 204 in the computer-readable file 142. As will be described in greater detail below, the map portion 206 identifies locations of the file records 202-204 in the computer-readable file 142. The computer-readable file 142 also comprises a read model 208 that is appended to the map portion 206. The read model 208 is configured to optimize retrievals when it is predicted that a read is likely. Furthermore, the computer-readable file 142 can comprise a file access portion 210 appended to the read model 208. The file access portion 210 includes at least one attribute for at least one user that has permission to access the computer-readable file 142. For instance, the file access portion 210 can identify one or more enterprises, wherein employees in such enterprise(s) are able to access the file 142.

Figure 3:
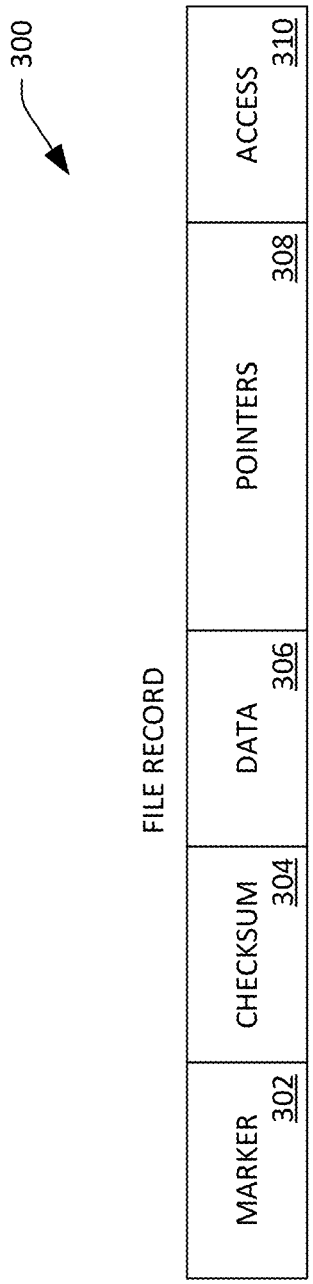
FIG. 3 is a schematic of an exemplary file record in a computer-readable file.

Now referring to FIG. 3, a schematic of an exemplary file record 300 that can be included in the computer-readable file 142 is illustrated. The file record 300 comprises data 306 about a patient encounter. The file record 300 additionally comprises a pointer portion 308. The pointer portion 308 is an area reserved for pointers to child file records of the file record 300 within the computer-readable file 142. When the file record 300 is initially created and appended to the computer-readable file 142, the pointer portion 308 does not yet contain pointers. However, as additional file records related to the data 306 are added to the computer-readable file 142, the file creation system 138 can update the pointer portion 308 to include pointers to the additional file records.

The file record 300 may also comprise a checksum 304 for the file record 300, where the checksum is over at least the data 306. Generally, the checksum 304 is used when the computer-readable file 142 is read to ensure lack of corruption of the computer-readable file 142. Additionally, the checksum 306 can further be used to skip file records when the computer-executable 142 is read by a computer-processor. The file record 300 also comprises a marker 302, wherein the marker 302 indicates a beginning of the file record 300.

Furthermore, the file record 300 comprises an access portion 310. The access portion 310 comprises one or more attributes of one or more users that have permission to access the data 306. For instance, the attribute could be an identifier for a particular healthcare organization, a particular healthcare professional, a particular insurance company, etc.

While the file record 300 is arranged in the manner shown in FIG. 3, with the marker 308 being at a beginning of the file record 300, the checksum 304 being immediately after the marker 302, the data 306 being immediately after the checksum 304, the pointer portion 308 being immediately after the data 306, and the access portion 310 being immediately after the pointer portion 308, it is to be noted that other arrangements are contemplated.

Figure 4:
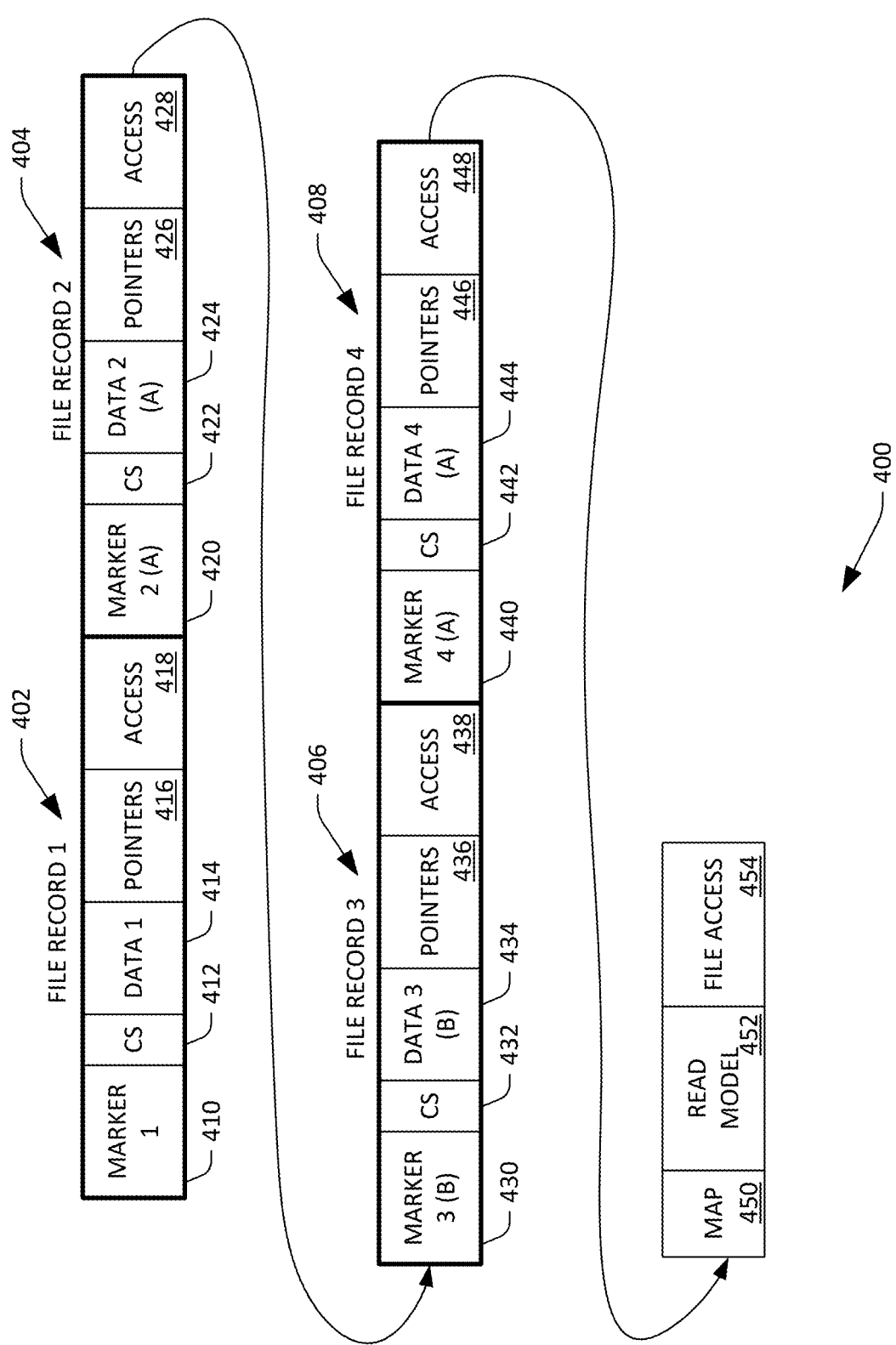
FIG. 4 is a schematic of an exemplary computer-readable file that comprises four file records.

With reference to FIG. 4, an exemplary computer-readable file 400 is illustrated. The computer-readable file 400 comprises four file records 402, 404, 406, and 408. The first file record 402 comprises a first marker 410, a first checksum 412, first data 414, a first pointer portion 416, and a first access portion 418. The second file record 404 comprises a second marker 420, a second checksum 422, second data 424, a second pointer portion 426, and a second access portion 428. The third file record 406 includes a third marker 430, a third check sum 432, third data 434, a third pointer portion 436, and a third access portion 438. The fourth file record 408 includes a fourth marker 440, a fourth check sum 442, fourth data 444, a fourth pointer portion 446, and a fourth access portion 448.

The first file record 402 is at the beginning of the computer-readable file 400 and includes information about the identity of a patient. Thus, the first data 414 may comprise an identifier for the patient. As can be ascertained, the first file record 402 serves as the ultimate parent for the file records 402-408, that is, a computing device may access locations within the computer-readable file 400 identified by pointers in the first pointer portion 416, repeat this process for subsequent file records, and assuming the requisite access permissions are met for each file record with the computer-readable file 400, reproduce the entirety of the patient record contained within the computer-readable file 400.

In the computer-readable file 400, the second file record 404 corresponds to a record generated as a result of a patient encounter for a first matter (A), whereas the third file record 406 corresponds to a record generated as a result of a patient encounter for a second matter (B). For instance, the first file record 402 can store data generated during an orthopedics appointment at a first healthcare facility and the second file record 404 can store data generated during an allergist appointment at a second healthcare facility. The fourth file record 408 corresponds to a record generated as a result of a follow-up appointment for the first matter (A). Thus, in the computer-readable file 400, the first pointer portion 416 of the first file record 402 comprises a pointer to the second file record 404 and a pointer to the third file record 406. The second pointer portion 426 of the second file record 404 comprises a pointer to the fourth file record 408. The pointer portion 436 of the third file record 406 and the pointer portion 446 of the fourth file record 408 are empty as no child file records currently exist for the third file record 406 and the fourth file record 408.

The computer-readable file 400 also includes a map portion 450, which will be described in greater detail below. Additionally, the computer-readable file 400 includes read model 452 as described above. Furthermore, the computer-readable file 400 comprises a file access portion 454. As described above, the file access portion 454 comprises one or more attributes of one or more users that has permission to access one or more file records of the computer-readable file 400. It is understood that the attributes within the file access portion 454, the first access portion 418, the second access portion 428, the third access portion 438, and the fourth access portion 448 may differ such that different users have access to different portions of the computer-readable file 400. For instance, the file access portion 454 may include an identifier for a healthcare organization so that a member of the healthcare organization can access the computer-readable file 400, but the access portions 418, 428, 438, and 448 may specify attributes of particular individuals within the healthcare organization that can access the file records 402-408.

Figure 5:
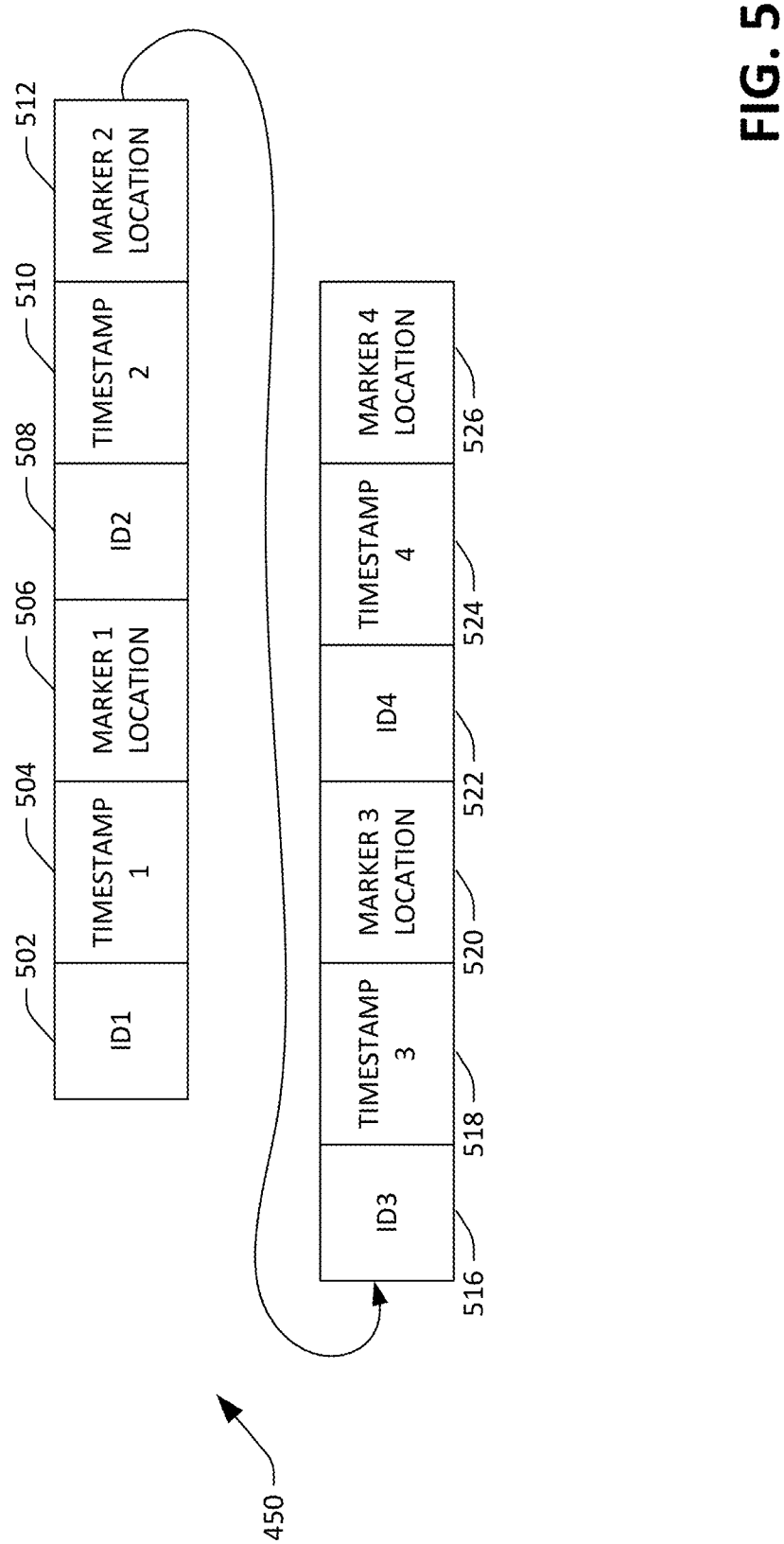
FIG. 5 is a schematic of a map portion of the computer-readable file shown in FIG. 4.

Turning now to FIG. 5, a schematic of the map portion 450 of the file 400 is illustrated. The map portion 450 includes an identifier 502 of the first file record 402, a timestamp 504 corresponding to the first file record 402, and a location 506 of the marker 410 of the first file record 402 in the computer-readable file 400. The map portion 450 may also include an identifier 508 of the second file record 404, a timestamp 510 corresponding to the second file record 404, and a location 512 of the marker 420 of the second file record 404 in the computer-readable file 400. The map portion 450 may additionally include an identifier 516 of the third file record 406, a timestamp 518 corresponding to the third file record 406, and a location 520 of the marker 430 of the third file record 406 in the computer-readable file 400. Finally, the map portion 450 may include an identifier 522 of the fourth file record 408, a timestamp 524 corresponding to the fourth file record 408, and a location 526 of the marker 440 of the fourth file record 408 in the computer-readable file 400.

The map portion 450 is accessed when the computer-readable file 400 is read. Specifically, a healthcare worker may wish to retrieve patient encounter data represented by the fourth file record 408 in the computer-readable file 400. To retrieve such patient encounter data, the healthcare worker can employ a client computing device to set forth a query, wherein the query identifies the fourth file record 408 in the computer-readable file 400. The client computing device can then transmit the query to a server computing device executing an EHR. In response to receipt of the query, the EHR can seek to the end of the computer-readable file 400. As a preliminary step, the EHR can verify that the healthcare worker has permission to access the compute-readable file 400 by examining the file access portion 454. For instance, the EHR may compare credentials of the healthcare worker to attributes stored in the file access portion 454.

After verifying that the healthcare worker has permission to access the computer-readable file 400, the EHR may seek to the read model 452, which optimizes retrievals when it is predicted that a read by the EHR is likely. The EHR may then seek to the map portion 450 of the computer-readable file 400. Using the map portion 450, the EHR can identify the identifier 522 of the fourth file record 404, and can further ascertain the location 526 of the marker 440 for the fourth file record 408. The EHR may then seek to the marker 440 in the computer-readable file 400. The EHR can verify that the healthcare worker has permission to access the fourth file record 408 by examining the access portion 448 for the fourth file record 408. For instance, the EHR may compare credentials of the healthcare worker to attributes stored in the access portion 448. After verifying that the healthcare worker has access to the fourth file record 408, the EHR can then transmit the fourth data 444 to the client computing device.

Alternatively, the EHR may access the fourth file record 404 starting from the first file record 402 by accessing pointers within the first pointer portion 416. The EHR can identify the identifier 502 of the first file record 402, and can further ascertain the location 506 of the marker 410 for the first file record 402. The EHR may then seek to the marker 410 in the computer-readable file 400. The EHR can verify that the healthcare worker has permission to access the first file record 402 using the first access portion 418 as described above. The EHR can then access the first data 414 and examine the first pointer portion 416 of the computer-readable file 400. As the first pointer portion 416 includes a pointer to the second file record 404, the EHR can seek to the second marker 420 of the second file record 404. After verifying the healthcare worker using the access portion 428, the EHR can then access the second data 424 and examine the second pointer portion 426 of the computer-readable file 400. As the second pointer portion 426 includes a pointer to the fourth file record 408, the EHR can seek to the fourth marker 440 of the fourth file record 408. After verifying the healthcare worker using the access portion 448, the EHR can transmit the fourth data 444 to the client computing device.

Figure 6:
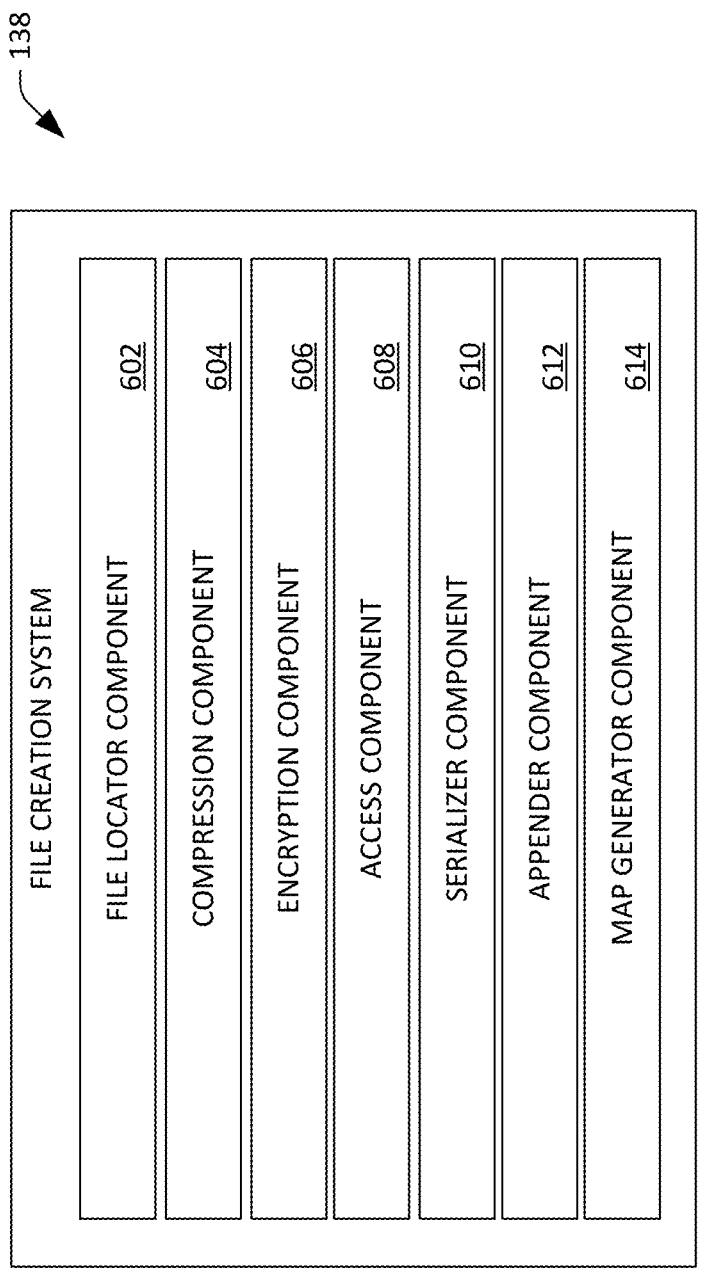
FIG. 6 is a functional block diagram of an exemplary file creation system.

Now referring to FIG. 6, a functional block diagram of the file creation system 138 is illustrated. The file creation system 138 includes a file locator component 602 that is configured to search the file store 140 for a computer-readable file for a patient in response to receiving data about the patient from one of the client computing devices 116 or 150. When the file locator component 602 determines that a computer-readable file already exists for the patient in the file store 140, the file location component 602 retrieves the computer-readable file from the file store so that the computer-readable file can be modified by appending a new file record to the computer-readable file. Additionally, the file locator component 602 can identify a parent file record in the computer-readable file for the data about the patient received from one of the client computing devices 116 or 150. When the file locator component 602 is unable to locate a computer-readable file for the patient in the file store 140, the file creation system 138 can create a new computer-readable file for the patient (as described above).

The file creation system 138 optionally also includes a compression component 604 that is configured to compress and/or decompress computer-readable files. For example, computer-readable files in the file store 140 may be compressed. Therefore, when the file locator component 602 identifies that a computer-readable file exists for the patient in the file store 140, the compression component 604 can decompress the computer-readable file, such that a new file record is able to be appended to the computer-readable file. The file creation system 138 may also include an encryption component 606 that is configured to encrypt/decrypt computer-readable files. Computer-readable files in the file store 140 may be encrypted, hence, when the file locator component 602 determines that a computer-readable file exists for the patient, the encryption component 606 can decrypt the computer-readable file, such that a new record can be appended to the computer-readable file.

The file creation system 138 also includes an access component 608 that is configured to place access restrictions on both the computer-readable file as a whole (in a file access portion), as well as individual file records within the computer-readable file (in an access portion). Thus, the access component 608 may create and/or modify the computer-readable file by specifying at least one attribute of a user that has permission to access the computer-readable file and/or file records within the computer-readable file. The file creation system 138 can also include a serializer component 610 that is configured to serialize and/or deserialize data. For example, files in the file store 140 may be serialized for storage purposes. When the file locator component 602 determines that a file exists for the patient (and subsequent to the computer-readable file being decompress and/or decrypted), the serializer component 610 can deserialize the computer-readable file.

An appender component 612 may then create a file record that includes 1) the data received from the client computing device 116 or the second client computing device 150; 2) at least one attribute of a user that has permission to access the computer-readable file; and 3) a pointer portion (initially empty). As described above, the appender component 612 may also include a marker and/or a checksum in the file record. The file creation system 138 also includes a map generator component 614 that generates or updates a map portion of the computer-readable file and appends the map portion to the last file record in the computer-readable file. The map generator component 614 can also generate pointers that can be stored in a pointer portion of a parent file record for the file record after the appender component 612 has appended the file record to the computer-readable file. The serializer component 610 may then serialize the computer-readable file, the encryption component 606 can encrypt the computer-readable file, and the compression component 604 can compress the computer-readable file (the order of these actions may differ). The file creation system 138 can then cause the computer-readable file to be stored in the file store 140.

Figure 7:
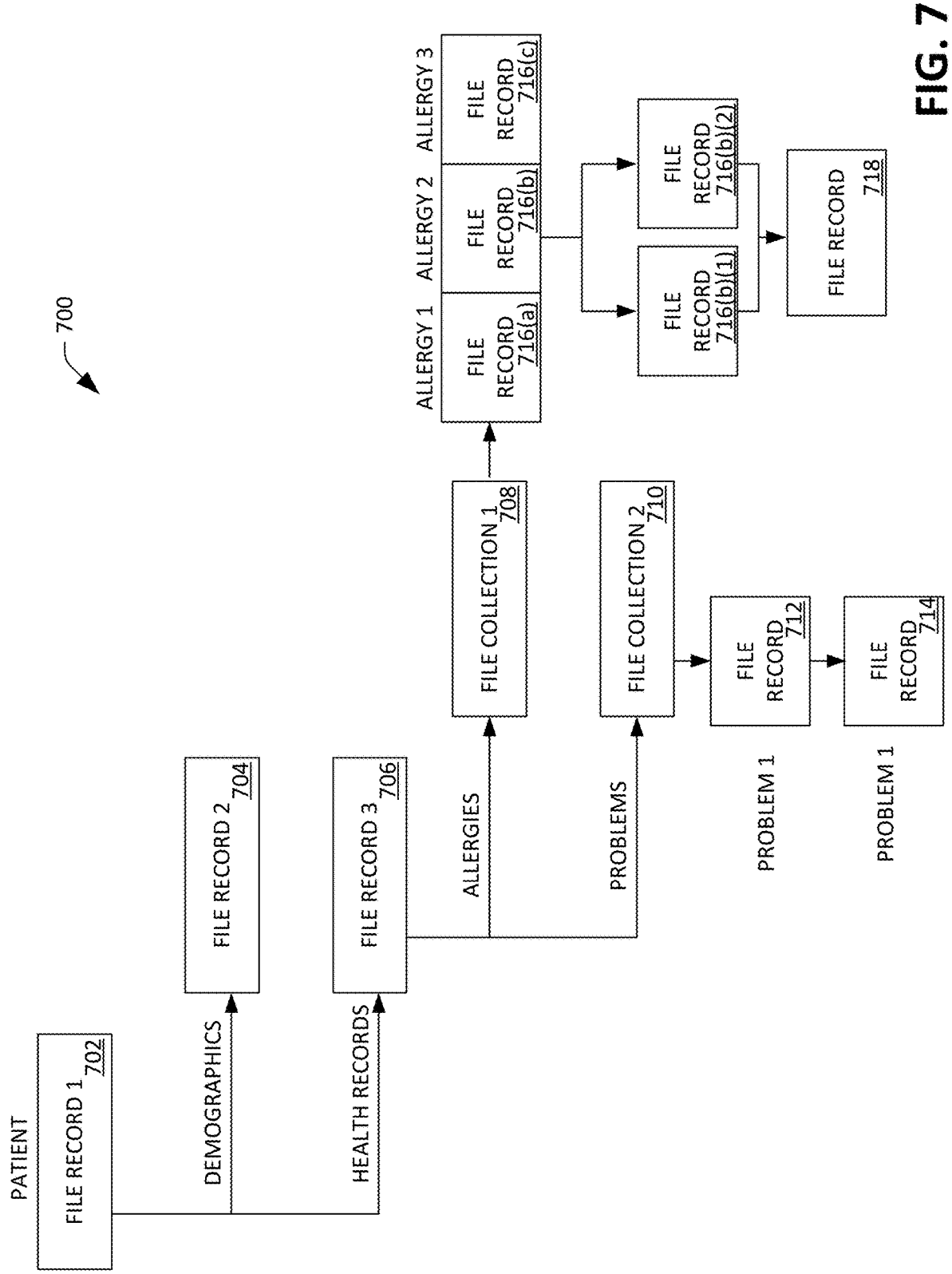
FIG. 7 is a schematic of parent-child relationships in an exemplary computer-readable file.

With reference to FIG. 7, a schematic of a computer-readable file 700 generated by the file creation system 138 of the EHR 110 depicting parent-child relationships between file records is illustrated. As can be ascertained from FIG. 7, the computer-readable file 700 can include "nested" file records and file collections that can be decomposed into constituent file records and/or file collections. The computer-readable file 700 comprises a first file record 702 corresponding to a patient. The first file record 702 serves as a top-level file record for all subsequent file records added to the computer-readable file 700. The first file record 702 includes a pointer to a second file record 704 corresponding to demographics for the patient (e.g., address, phone number, sex, etc.) and a third file record 706 corresponding to the health records of the patient.

The third file record 706 includes a pointer to a first file collection 708, corresponding to patient allergies, and a pointer to a second file collection 710, corresponding to patient problems. A file collection is a file record that includes data indicative of a category (e.g., allergies, problems) and pointers to file records that belong to the category (e.g., allergy 1, allergy 2, problem 1, problem 2, etc.). The first file collection 708 includes pointers to three child file records: a file record 716(a), a file record 716(b), and a file record 716(c), corresponding to a first allergy, a second allergy, and a third allergy, respectively.

File records within the computer-readable file 700 may be "forked" such that independent records of the same underlying healthcare issue can exist simultaneously within the computer-readable file 700. For instance, a patient diagnosed may be diagnosed with allergy 2 by his or her primary healthcare professional. A client computing device operated by the primary healthcare professional can transmit data indicative of this diagnosis to the EHR 110 and the file creation system 138 of the EHR 110 can cause the file record 716(*b*) to be appended to the computer-readable file 700. After appending the file record 716(*b*) to the computer-readable file 700, the file creation system 138 can update a pointer portion of the first file collection 708 to include a pointer to the file record 716(*b*).

The patient may then decide to obtain an opinion on allergy 2 from a first allergist, thus leading to a first patient encounter. A client computing device operated by the first allergist may download the computer-readable file 700 and read the data contained in the file record 716(*b*). The first allergist may review the data in the file record 716(*b*) in order to treat the patient. The client computing device operated by the first allergist may also receive data inputted by the first allergist reflective of the first patient encounter. The client computing device operated by the first allergist may transmit this data to the EHR 110 executing on the server computing device 132. In an example, the patient may decide that he or she does not want the data reflective of the first patient encounter to be accessible to other healthcare professionals. The file creation system 138 of the EHR 110 can then generate a file record 716(*b*)(1) for the first patient encounter (including access restrictions) and append the file record 716(*b*)(1) to the computer-readable file 700. After appending the file record 716(*b*)(1) to the computer-readable file 700, the file creation system 138 can update a pointer portion of the file record 716(*b*) to include a pointer to the file record 716(*b*)(1).

Subsequent to the first patient encounter with the first allergist, the patient may then decide to obtain an opinion on allergy 2 from a second allergist, thus leading to a second patient encounter. A client computing device operated by the second allergist may access the computer-readable file 700 and read the data contained in the file record 716(*b*). The second allergist may review the data in the file record 716(*b*) in order to treat the patient. The client computing device operated by the second allergist may also receive data inputted by the second allergist that is indicative of the second patient encounter. The client computing device operated by the second allergist may transmit this data to the EHR 110 executing on the server computing device 132. The file creation system 138 of the EHR 110 can then generate a file record 716(*b*)(2) for the second patient encounter and append the file record 716(*b*)(2) to the computer-readable file 700. After appending the file record 716(*b*)(2) to the computer-readable file 700, the file creation system 138 can update a pointer portion of the file record 716(*b*) to include a pointer to the file record 716(*b*)(2).

Sometime thereafter, the patient may decide to obtain an opinion on allergy 2 from a third allergist, leading to a third patient encounter. Moreover, the patient may decide that he or she wants the first allergist and the second allergist to have access to any data generated during the visit with the third allergist. A client computing device operated by the third allergist may download the computer-readable file 700 and read the data contained in the fire record 716(*b*), the file record 716(*b*)(1), and the file record 716(*b*)(2). The third allergist may then review data contained in these file records. The client computing device operated by the third allergist may also receive input from the third allergist reflective of the third patient encounter. The client computing device operated by the third allergist may then transmit data reflective of the input to the EHR 110 executing on the server computing device 132. The file creation system 138 of the EHR 110 can then generate a file record 718 for the third patient encounter and append the file record 718 to the computer-readable file 700. Responsive to appending the file record 718 to the computer-readable file 700, the file creation system 138 can update a pointer portion of the file record 716(*b*)(1) to include a pointer to the file record 718. Likewise, the file creation system can also update a pointer portion of the file record 716(*b*)(2) to include a pointer to the file record 718. Thus, both the second allergist and the third allergist will have access to data in the file record 718.

In the example shown in FIG. 7, the second file collection 710 comprises a file record 712 corresponding to a first problem, for example shortness of breath. A client computing device operated by the primary healthcare professional can transmit data indicative of a patient encounter related to the shortness of breath issue to the EHR 110 executing on the server computing device 132, wherein the file creation system 138 of the EHR 110 can generate a file record 712 reflective of this patient encounter. The file creation system 138 can also store a pointer to the file record 712 in the second file collection 710. Subsequently, the patient may have a follow-up visit for the shortness of breath issue with the primary healthcare professional. The client computing device can transmit data indicative of the follow-up patient encounter to the EHR 110, wherein the file creation system 138 can then generate a file record 714 indicative of this encounter and append the file record 714 to the computer-readable file 700. The file creation system 138 may store a "diff" for data, that is, the file creation system 138 may store data in the file record 714 that is not duplicative of the data in the file record 712. The file creation system 138 can then store a pointer to the file record 714 in a pointer portion of the file record 712.

Figure 8:
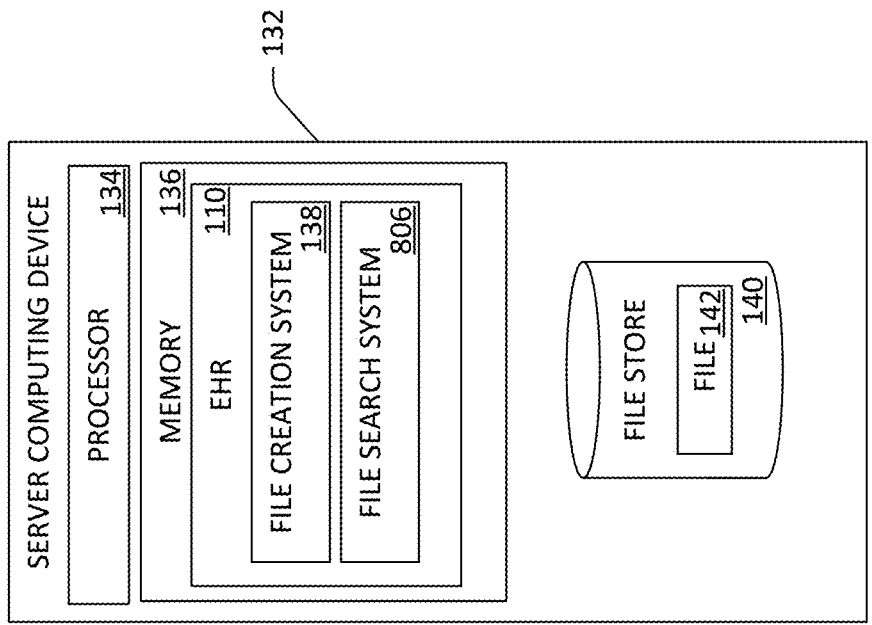
FIG. 8 is a functional block diagram of an exemplary system that facilitates transmission of a computer-readable file to a client computing device in response to receipt of a query.
Figure 8:
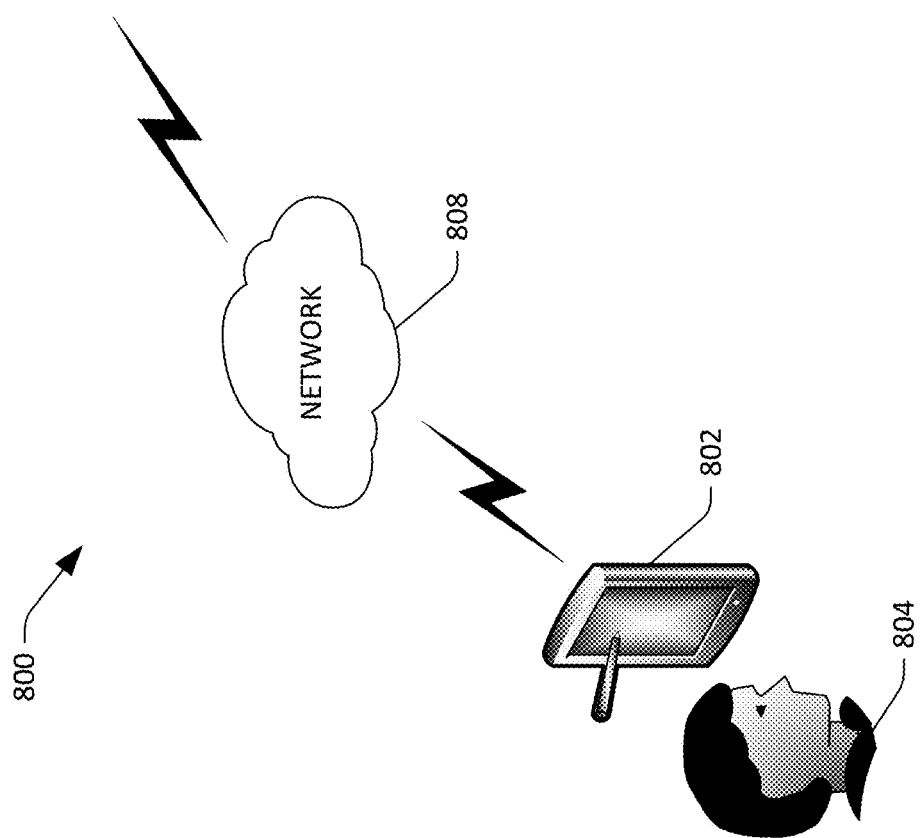

Now referring to FIG. 8, an exemplary system 800 that facilitates transmitting at least a portion of a computer-readable file 142 to a requesting client computing device is illustrated. The system 800 includes a client computing device 802 employed by a healthcare worker 804, wherein the client computing device 802 is in communication with the server computing device 132 by way of a network 808 (e.g., the Internet). The healthcare worker 804 employs the client computing device 802 to generate a request for at least a portion of the computer-readable file 142 and transmits the request to the EHR 110 executing on the server computing device 132. The EHR 110 includes a file search system 806 that can access the file store 140. The file search system 806, in response to receiving the request for the portion of the computer-readable file 142 from the client computing device 802, identifies the computer-readable file 142 and transmits data from the requested portion of the computer-readable file 142 to the client computing device 802 by way of the network 808. The client computing device 802, therefore has access to the requested information from within the file 142.

It can be ascertained that the technologies described present various advantage compared to the conventional data storage paradigm for EHRs. First, since the file record system described above can be configured to store differences between subsequent file entries, files can be stored using less storage space than conventional data storage. Second, the technologies described above facilitate efficient transmission of patient records (as the entirety of a patient record is stored in a single computer-readable file) while maintaining patient privacy (as different file records may have access portions which restrict access to certain users).

Third, the technologies described above eliminate the problem of "silos" by keeping health records of a patient in a single computer-readable file that can be accessed by different healthcare organizations.

Figure 9:
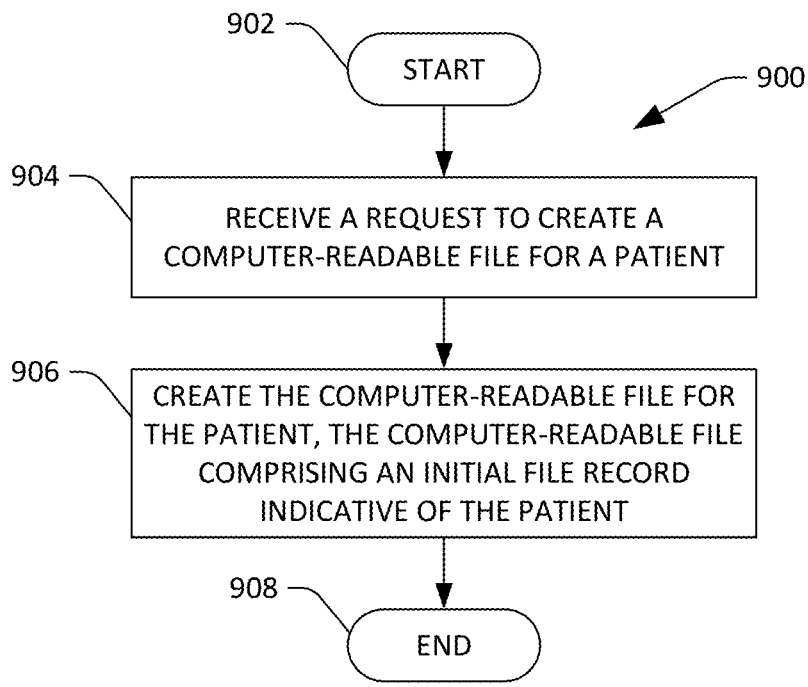
FIG. 9 is a flow diagram illustrating an exemplary methodology for creating a computer-readable file for a patient.
Figure 10:
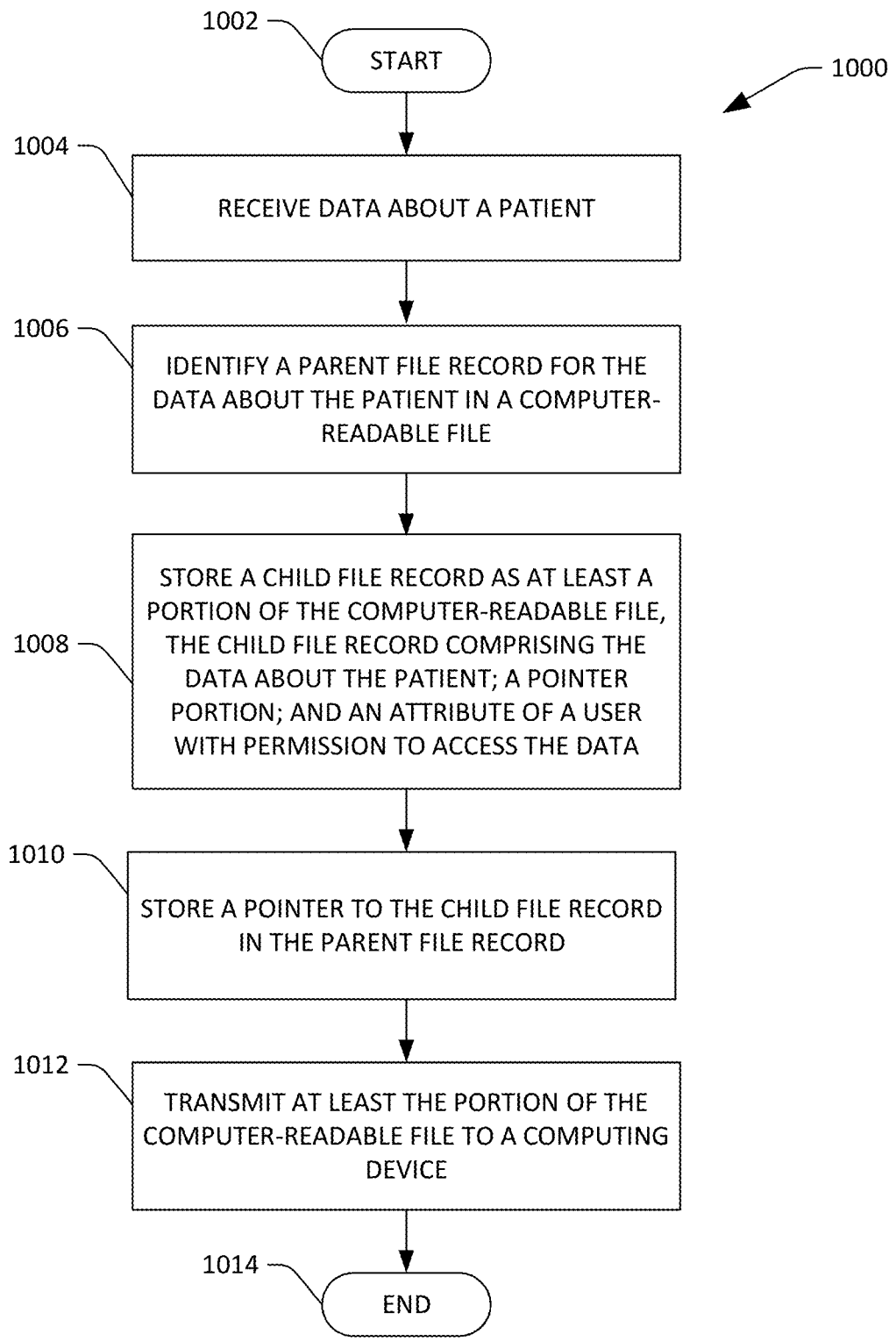
FIG. 10 is a flow diagram illustrating an exemplary methodology for modifying a computer-readable file for a patient.
Figure 11:
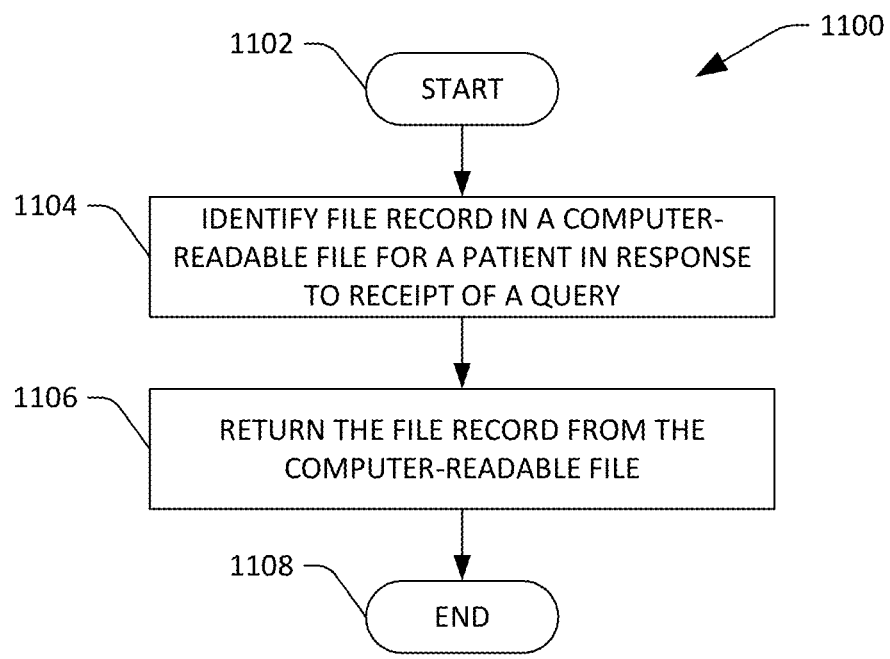
FIG. 11 is a flow diagram illustrating an exemplary methodology for locating a file record in a computer-readable file.

FIGS. 9-11 illustrate exemplary methodologies relating to creating and modifying computer-readable files, as well as locating records in computer-readable files. While the methodologies are shown and described as being a series of acts that are performed in a sequence, it is to be understood and appreciated that the methodologies are not limited by the order of the sequence. For example, some acts can occur in a different order than what is described herein. In addition, an act can occur concurrently with another act. Further, in some instances, not all acts may be required to implement a methodology described herein.

Moreover, the acts described herein may be computer-executable instructions that can be implemented by one or more processors and/or stored on a computer-readable medium or media. The computer-executable instructions can include a routine, a sub-routine, programs, a thread of execution, and/or the like. Still further, results of acts of the methodologies can be stored in a computer-readable medium, displayed on a display device, and/or the like.

Referring now to FIG. 9, a methodology 900 executed by an EHR that facilitates creating a computer-readable file is illustrated. The methodology 900 begins at 902, and at 904, a request to create a computer-readable file for a patient is received by the EHR. The request is received from a client computing device. At 906, the EHR creates the computer-readable file for the patient, the computer-readable file comprising an initial file record that includes an identifier of the patient. As described above, the initial file record can include a pointer portion, wherein the pointer portion can be subsequently amended to include pointers to records that are later added to the computer-readable file. The methodology 900 concludes at 908.

With reference now to FIG. 10, a methodology 1000 executed by a server computing device that facilitates modifying a computer-readable file for a patient is illustrated. The methodology 1000 begins at 1002, and at 1004, the server computing device receives data about a patient (e.g., from a client computing device in network communication with the server computing device). At 1006, the computing system identifies a parent file record for the child file record. The parent file record is located in a computer-readable file stored in a computer-readable storage device of the server computing device. At 1008, a child file record is stored in the computer-readable storage device as at least a portion of the computer-readable file. The child file record comprises the data about the patient; an initially empty pointer portion that can later be modified to include pointers to subsequent file records; and an attribute of a user that has permission to access the data about the patient. At 1010, the computing system stores a pointer to the child file record in the parent file record. At 1012, the computing system transmits at least the portion of the computer-readable file to a computing device (e.g., a client computing device) over a network connection. The methodology 1000 concludes at 1014.

Turning now to FIG. 11, a methodology 1100 that facilitates locating a file record in a computer-readable file is illustrated. The methodology 1100 begins at 1102, and at 1104 a file record in the computer-readable patient file is located in response to receipt of a query. As described previously, the query can identify at least one file record in the computer-readable file. The file record can be identified based upon analysis of the map portion of the computer-readable file for the patient. At 1106, the file record is returned. The methodology 1100 concludes at 1108.

Figure 12:
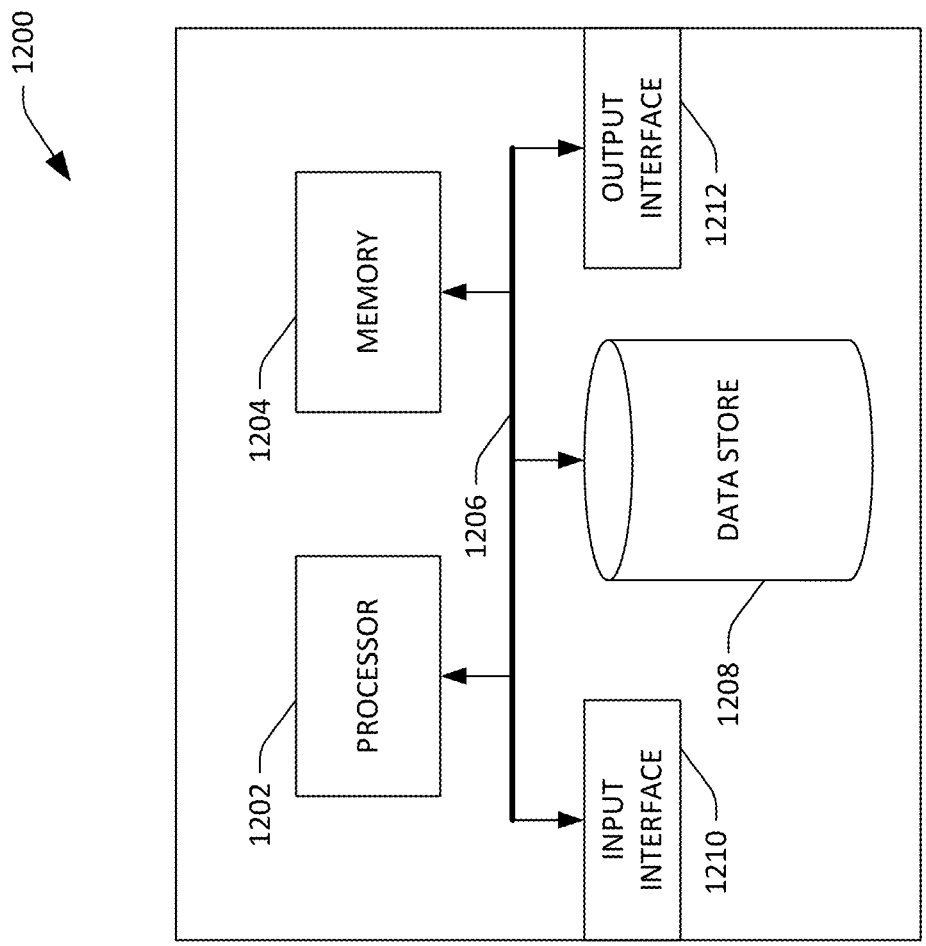
FIG. 12 is an exemplary computing system.

Referring now to FIG. 12, a high-level illustration of an exemplary computing device 1200 that can be used in accordance with the systems and methodologies disclosed herein is illustrated. For instance, the computing device 1200 may be used in a system that is configured to create and/or modify a computer-readable file. By way of another example, the computing device 1200 can be used in a system that is configured to search over contents of a computer-readable file. The computing device 1200 includes at least one processor 1202 that executes instructions that are stored in a memory 1204. The instructions may be, for instance, instructions for implementing functionality described as being carried out by one or more components discussed above or instructions for implementing one or more of the methods described above. The processor 1202 may access the memory 1204 by way of a system bus 1206. In addition to storing executable instructions, the memory 1204 may also store data about patients, including files, file records, etc.

The computing device 1200 additionally includes a data store 1208 that is accessible by the processor 1202 by way of the system bus 1206. The data store 1208 may include executable instructions, patient files, etc. The computing device 1200 also includes an input interface 1210 that allows external devices to communicate with the computing device 1200. For instance, the input interface 1210 may be used to receive instructions from an external computer device, from a user, etc. The computing device 1200 also includes an output interface 1212 that interfaces the computing device 1200 with one or more external devices. For example, the computing device 1200 may display text, images, etc. by way of the output interface 1212.

It is contemplated that the external devices that communicate with the computing device 1200 via the input interface 1210 and the output interface 1212 can be included in an environment that provides substantially any type of user interface with which a user can interact. Examples of user interface types include graphical user interfaces, natural user interfaces, and so forth. For instance, a graphical user interface may accept input from a user employing input device(s) such as a keyboard, mouse, remote control, or the like and provide output on an output device such as a display. Further, a natural user interface may enable a user to interact with the computing device 1200 in a manner free from constraints imposed by input device such as keyboards, mice, remote controls, and the like. Rather, a natural user interface can rely on speech recognition, touch and stylus recognition, gesture recognition both on screen and adjacent to the screen, air gestures, head and eye tracking, voice and speech, vision, touch, gestures, machine intelligence, and so forth.

Additionally, while illustrated as a single system, it is to be understood that the computing device 1200 may be a distributed system. Thus, for instance, several devices may be in communication by way of a network connection and may collectively perform tasks described as being performed by the computing device 1200.

Various functions described herein can be implemented in hardware, software, or any combination thereof. If implemented in software, the functions can be stored on or transmitted over as one or more instructions or code on a computer-readable medium. Computer-readable media includes computer-readable storage media. A computer-readable storage media can be any available storage media that can be accessed by a computer. By way of example, and not limitation, such computer-readable storage media can comprise RAM, ROM, EEPROM, CD-ROM or other optical disk storage, magnetic disk storage or other magnetic storage devices, or any other medium that can be used to carry or store desired program code in the form of instructions or data structures and that can be accessed by a computer. Disk and disc, as used herein, include compact disc (CD), laser disc, optical disc, digital versatile disc (DVD), floppy disk, and blu-ray disc (BD), where disks usually reproduce data magnetically and discs usually reproduce data optically with lasers. Further, a propagated signal is not included within the scope of computer-readable storage media. Computer-readable media also includes communication media including any medium that facilitates transfer of a computer program from one place to another. A connection, for instance, can be a communication medium. For example, if the software is transmitted from a website, server, or other remote source using a coaxial cable, fiber optic cable, twisted pair, digital subscriber line (DSL), or wireless technologies such as infrared, radio, and microwave, then the coaxial cable, fiber optic cable, twisted pair, DSL, or wireless technologies such as infrared, radio and microwave are included in the definition of communication medium. Combinations of the above should also be included within the scope of computer-readable media.

Alternatively, or in addition, the functionally described herein can be performed, at least in part, by one or more hardware logic components. For example, and without limitation, illustrative types of hardware logic components that can be used include Field-programmable Gate Arrays (FPGAs), Program-specific Integrated Circuits (ASICs), Program-specific Standard Products (ASSPs), System-on-a-chip systems (SOCs), Complex Programmable Logic Devices (CPLDs), etc.

What has been described above includes examples of one or more embodiments. It is, of course, not possible to describe every conceivable modification and alteration of the above devices or methodologies for purposes of describing the aforementioned aspects, but one of ordinary skill in the art can recognize that many further modifications and permutations of various aspects are possible. Accordingly, the described aspects are intended to embrace all such alterations, modifications, and variations that fall within the spirit and scope of the appended claims. Furthermore, to the extent that the term "includes" is used in either the details description or the claims, such term is intended to be inclusive in a manner similar to the term "comprising" as "comprising" is interpreted when employed as a transitional word in a claim.

What is claimed is:

1. A method, comprising:
in response to receiving data about a patient generated by an electronic health record application (EHR), modifying a computer-readable file for the patient, the computer-readable file stored in a computer-readable storage device, wherein the computer-readable file comprises a plurality of file records that are appended to one another within the computer-readable file based upon respective times of creation of each of the plurality of file records, wherein modifying the computer-readable file is performed by a computer processor of a computing system, and wherein modifying the computer-readable file comprises:
identifying a parent file record for the data about the patient from amongst the plurality of file records located in the computer-readable file;
appending a child file record to a most recently added file record in the plurality of file records of the computer-readable file, the child file record comprising:
the data about the patient;
a pointer portion, wherein the pointer portion is initially empty, wherein the pointer portion is later populated with pointers to subsequently added child file records of the child file record; and
an attribute of a healthcare worker that has permission to access the data about the patient comprised by the child file record stored within the computer-readable file;
storing a pointer to the child file record in the parent file record, wherein the pointer points to the data about the patient comprised by the child file record within the computer-readable file; and
transmitting at least a portion of the computer-readable file to a client computing device in response to receiving a query from the client computing device, wherein the client computing device is in network communication with the computing system.

2. The method of claim 1, further comprising:
in response to receiving second data about the patient generated by the EHR, modifying the computer-readable file for the patient, wherein modifying the computer-readable file comprises:
identifying the parent file record;
appending a second child file record to the computer-readable file, the second child file record comprising:
the second data about the patient;
a second pointer portion, wherein the second pointer portion is initially empty, wherein the second pointer portion is later populated with pointers to subsequently added child file records of the second child file record; and
an attribute of a second healthcare worker that has permission to access the second data about the patient; and
storing a second pointer to the second child file record in the parent file record, wherein the second pointer points to the second data about the patient.

3. The method of claim 2, wherein the attribute of the healthcare worker differs from the attribute of the second healthcare worker.

4. The method of claim 2, wherein the child file record of the computer-readable file further comprises:
a first marker that identifies a beginning of the child file record; and
wherein the second child file record of the computer-readable file further comprises:
a second marker that identifies a beginning of the second child file record.

5. The method of claim 2, wherein the child file record of the computer-readable file further comprises:
a first checksum over at least the data about the patient; and
wherein the second child file record of the computer-readable file further comprises:
a second checksum over at least the second data about the patient.

6. The method of claim 2, wherein modifying the computer-readable file further comprises:
appending a read model to the computer-readable file, wherein the read model is configured to optimize retrieval of content of the computer-readable file when it is predicted that a read is likely.

7. The method of claim 2, wherein modifying the computer-readable file further comprises:
appending a file access portion to the computer-readable file, wherein the file access portion comprises an attribute of at least one user that has permission to access the computer-readable file.

8. The method of claim 2, wherein modifying the computer-readable file further comprises:
subsequent to appending the child file record to the most recently added file record, appending a map portion to the child file record of the computer-readable file, the map portion comprising:
a location of the child file record in the computer-readable file; and
a location of the second child file record in the computer-readable file.

9. The method of claim 8, wherein the map portion further comprises:
a first timestamp indicative of when the EHR generated the first data about the patient; and
a second timestamp indicative of when the EHR generated the second data about the patient.

10. The method of claim 1, further comprising:
responsive to modifying the computer-readable file and prior to transmitting the at least a portion of the computer-readable file, at least one of encrypting or compressing the computer-readable file.

11. The method of claim 1, further comprising:
responsive to receiving the data about the patient, serializing the data about the patient prior to appending the child file record to the most recently added file record in the computer-readable file.

12. The method of claim 1, further comprising:
in response to receiving second data about the patient generated by the EHR, wherein the second data about the patient is a modified version of the first data about the patient, modifying the computer-readable file for the patient, wherein modifying the computer-readable file comprises:
identifying a parent file record for the second data about the patient, the parent file record located in the computer-readable file, wherein the parent file record for the second data about the patient is the child file record, wherein the second data about the patient comprises a first portion and a second portion, wherein the first portion is duplicative to the first data, wherein the second portion is not duplicative to the first data;
responsive to identifying the parent file record for the second data about the patient, appending a second child file record to the computer-readable file, the second child file record comprising:
a diff, wherein the diff contains the second portion comprised by the second data about the patient;
a second pointer portion, wherein the second pointer portion is initially empty, wherein the second pointer portion is later populated with pointers to subsequently added child file records of the second child file record;
an attribute of a second healthcare worker that has permission to access the diff; and
storing a second pointer to the second child file record in the parent file record for the second data about the patient, wherein the second pointer points to the diff.

13. A computing system comprising:
a processor; and
memory that stores instructions that, when executed by the processor, cause the at least one processor to perform acts comprising:
modifying a computer-readable file for a patient in response to receiving data about the patient generated by an electronic health record application (EHR), wherein the computer-readable file comprises a plurality of file records that are appended to one another within the computer-readable file based upon respective times of creation of each of the plurality of file records, wherein modifying the computer-readable file comprises:
identifying a parent file record for the data about the patient from amongst the plurality of file records located in the computer-readable file;
generating a child file record for the data about the patient, the child file record comprising:
the data about the patient;
a pointer portion, wherein the pointer portion is initially empty, wherein the pointer portion is later populated with pointers to subsequently added child file records of the child file record; and
an attribute of a first healthcare worker that has permission to access the data about the patient comprised by the child file record;
appending the child file record to a mostly recently added file record in the plurality of file records of the computer-readable file;
storing a pointer to the child file record in the parent file record, wherein the pointer points to the data about the patient comprised by the child file record within the computer-readable file; and
transmitting at least a portion of the computer-readable file to a client computing device in response to receiving a query from the client computing device, wherein the client computing device is in network communication with the computing system.

14. The computing system of claim 13, the acts further comprising:
modifying the computer-readable file for the patient in response to receiving second data about the patient generated by the EHR, wherein modifying the computer-readable file comprises:
identifying the parent file record;
generating a second child file record for the second data about the patient, the second child file record comprising:
the second data about the patient;
a second pointer portion, wherein the second pointer portion is initially empty, wherein the second pointer portion is later populated with pointers to subsequently added child file records of the second child file record; and
an attribute of a second healthcare worker that has permission to access the second data about the patient;
appending the second child file record to the computer-readable file; and
storing a second pointer to the second child file record in the parent file record, wherein the second pointer points to the second data about the patient.

15. The computing system of claim 14, the acts further comprising:
appending a map portion to the computer-readable file, the map portion comprising:
a location of the child file record in the computer-readable file;

a first timestamp indicative of when the EHR generated the data about the patient;
a location of the second child file record in the computer-readable file; and
a second timestamp indicative of when the EHR generated the second data about the patient.

16. The computing system of claim 14, the acts further comprising:
appending a file access portion to the computer-readable file, wherein the file access portion comprises an attribute of at least one user that has permission to access the computer-readable file.

17. The computing system of claim 14, wherein the child file record of the computer-readable file further comprises:
a first marker that identifies a beginning of the child file record; and
wherein the second child file record of the computer-readable file further comprises:
a second marker that identifies a beginning of the second child file record.

18. The computing system of claim 14, wherein the child file record of the computer-readable file further comprises:
a first checksum over at least the data about the patient; and
wherein the second child file record of the computer-readable file further comprises:
a second checksum over at least the second data about the patient.

19. The computing system of claim 13, the acts further comprising:
modifying the computer-readable file for the patient in response to receiving second data about the patient generated by the EHR, wherein the second data about the patient is a modified version of the first data about the patient, wherein modifying the computer-readable file comprises:
identifying a parent file record for the second data about the patient, the parent file record for the second data about the patient located in the computer-readable file, wherein the parent file record for the second data about the patient is the child file record;
generating a second child file record for the second data about the patient, the second child file record comprising:
a diff, wherein the diff contains only data within the second data about the patient that is not duplicated in the first data about the patient;
a second pointer portion, wherein the second pointer portion is initially empty, wherein the second pointer portion is later populated with pointers to subsequently added child file records of the second child file record; and
an attribute of a second healthcare worker that has permission to access the diff appending the second child file record to the computer-readable file; and
storing a second pointer to the second child file record in the parent file record for the second data about the patient, wherein the second pointer points to the diff.

20. A non-transitory computer-readable storage medium comprising instructions that, when executed by a processor, cause the processor to perform acts comprising:
identifying a parent file record for first data about a patient from amongst a plurality of file records comprised by a computer-readable file, wherein the plurality of file records are appended to one another within the computer-readable file based upon respective times of creation of each of the plurality of file records, the first data about the patient generated by an electronic health record application (EHR);
identifying a parent file record for second data about the patient from amongst the plurality of file records, wherein the parent file record for the second data about the patient is the parent file record, the second data about the patient generated by the EHR;
modifying the computer-readable file to comprise:
a first child file record comprising:
the first data about the patient;
a first pointer portion, wherein the first pointer portion is initially empty, wherein the first pointer portion is later populated with pointers to subsequently added child file records of the first child file record; and
an attribute of a first healthcare worker that has permission to access the first data, wherein the first child file record is appended to a most recently added file record in the plurality of file records;
a second child file record comprising:
the second data about the patient;
a second pointer portion, wherein the second pointer portion is initially empty, wherein the second pointer portion is later populated with pointers to subsequently added child file records of the second child file record;
an attribute of a second healthcare worker that has permission to access the second data, wherein the second child file record is appended to the first child file record comprised by the computer-readable file;
a pointer to the first child file record, wherein the pointer to the first child file record is located in the parent file record;
a pointer to the second child file record, wherein the pointer to the second child file record is located in the parent file record; and
a map portion that identifies a location of the parent file record in the computer-readable file, a location of the first child file record in the computer-readable file, and a location of the second child file record in the computer-readable file; and
transmitting the computer-readable file to a client computing device in response to receiving a query from the client computing device.

\* \* \* \* \*